United States Patent
Breimesser et al.

(10) Patent No.: US 7,527,767 B2
(45) Date of Patent: May 5, 2009

(54) MICRO-FLUIDIC SYSTEM WITH SENSORS RESPECTIVELY ASSIGNED TO PLURAL FLUID PATHS

(75) Inventors: Fritz Breimesser, Nuremberg (DE); Joerg Hassel, Erlangen (DE); Ingeborg Lades, Erlangen (DE); Arno Steckenborn, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/910,467

(22) Filed: Aug. 4, 2004

(65) Prior Publication Data

US 2005/0054111 A1  Mar. 10, 2005

Related U.S. Application Data

(63) Continuation of application No. PCT/DE03/00278, filed on Jan. 31, 2003.

(30) Foreign Application Priority Data

Feb. 4, 2002  (DE) ............................... 102 04 414

(51) Int. Cl.
*B01L 3/02* (2006.01)
(52) U.S. Cl. ................. 422/100; 436/180; 204/601; 204/451; 422/99; 422/129
(58) Field of Classification Search .......... 422/99–101, 422/129; 436/180; 204/601, 451
See application file for complete search history.

(56) References Cited

U.S. PATENT DOCUMENTS

| 5,810,297 | A | 9/1998 | Basuthakur et al. |
| 6,001,231 | A | 12/1999 | Kopf-Sill |
| 6,086,740 | A | 7/2000 | Kennedy |
| 6,171,865 | B1 | 1/2001 | Weigl et al. |
| 6,488,895 | B1 * | 12/2002 | Kennedy ................. 422/100 |
| 2001/0052460 | A1 * | 12/2001 | Chien et al. ............. 204/450 |

FOREIGN PATENT DOCUMENTS

| DE | 34 30 288 A1 | 2/1986 |
| EP | 1 096 261 A2 | 5/2001 |
| EP | 1 123 734 A2 | 8/2001 |
| EP | 1 123 739 A1 | 8/2001 |
| WO | WO 01/29435 A1 | 4/2001 |
| WO | WO 01/41916 A1 | 6/2001 |

\* cited by examiner

*Primary Examiner*—Jill Warden
*Assistant Examiner*—Jyoti Nagpaul
(74) *Attorney, Agent, or Firm*—Sughrue Mion, PLLC

(57) ABSTRACT

To monitor functions in a micro-fluidic system having mutually similar parallel fluid paths, sensors (7) are assigned to the individual fluid paths (5) at the same respective locations, in order to measure a physical parameter that is influenced by the fluid stream in the fluid paths (5). The sensors (7) are connected to an evaluation device (10), which diagnoses a change in the operating state of the micro-fluidic system based on the differences in the parameters measured by the sensors (7).

9 Claims, 2 Drawing Sheets

MICRO-FLUIDIC SYSTEM WITH SENSORS RESPECTIVELY ASSIGNED TO PLURAL FLUID PATHS

This is a Continuation of International Application PCT/DE03/00278, with an international filing date of Jan. 31, 2003, which was published under PCT Article 21(2) in German, and the disclosure of which is incorporated into this application by reference.

FIELD AND BACKGROUND OF THE INVENTION

The invention relates to a micro-fluidic system with mutually similar fluid paths arranged in parallel with one another.

For chemical or biochemical analysis and synthesis processes, micro-fluidic systems promise vast improvements over macroscopic systems with respect to quality, speed and cost, because the reaction times and dwell times within the fluid paths are very short, only very small amounts of a substance are used, and these substances are processed very precisely and reproducibly. To satisfy the requirements regarding quantity, throughput and productivity, particularly in industrial applications, a possibly very large number of fluid paths must be connected in parallel (numbering up). Depending on the application, this parallel connection can be implemented by forming and parallel-connecting a plurality of similar micro-channels in micro-fluidic components, e.g., a mixer, or by multiply parallel-connecting entire micro-fluidic components or systems assembled from micro-fluidic components. With suitable micro-technology processes (e.g., etching processes, LIGA techniques or micro-mechanics) the parallel fluid paths can be produced in the same manner with great precision, such that the same process conditions, e.g., pressure, temperature, mass rate of flow, etc., are present in all the parallel-connected fluid paths. As a result, the same products can be obtained from all the parallel fluid paths and can be combined without any loss of quality.

However, micro-fluidic systems are subject to operational changes in the effective flow resistance due to both local fluctuations in the viscosity of the fluid and obstructions in the fluid paths, which can further change the operating conditions and cause progressive obstruction, resulting eventually in complete failure of the system. Whereas in macroscopic systems the mass flow rate, for example, can be readily measured with practically no interference and supplied to a flow control, the same cannot be achieved for the individual paths in parallelized micro-fluidic systems at a justifiable cost.

OBJECTS OF THE INVENTION

Thus, one object of the invention is to provide a system and/or a method that allows the functions of parallelized micro-fluidic systems to be monitored.

SUMMARY OF THE INVENTION

According to one formulation of the invention, this and other objects are attained by assigning sensors to the individual fluid paths at functionally comparable locations in the micro-fluidic system. These sensors are provided to measure physical or chemical parameters that are influenced by the fluid stream within the fluid paths. These sensors are connected to an evaluation unit, which diagnoses a change in the operating state of the micro-fluidic system based on deviations in the parameters measured by the sensors.

As used herein, the term "same locations" should be understood to mean equivalent locations relative to the parameter to be measured. For example, the flow rate of the fluid in a channel without a branch is the same everywhere, whereas the pressure may differ, e.g., because of a flow-related pressure drop. Therefore, the term "same location" would have differing interpretations in these two different measurement circumstances.

The term "physical parameters" encompasses, in particular, pressure, temperature and flow rate; and the term "chemical parameters" encompasses, for example, the pH value.

Because the fluid paths of the parallelized micro-fluidic system are formed in the same manner, the same process conditions exist in the undisturbed state of the system at the same respective locations in all the parallel fluid paths. As a result, the sensors measure the same value of the physical or chemical parameter. However, if one parameter differs in value from the other measured parameters, then this indicates a disturbance in the associated fluid path. Depending on the system or the application, different actions may then be triggered. For example, for safety reasons, the entire system or only the affected fluid path may be shut down, and a previously unused substitute fluid path may be added in place of the shut down fluid path. Another option is to introduce a purge process to eliminate the disturbance in the corresponding fluid path. If the process is to be continued without interruption, the process conditions can be changed by modifying global parameters, e.g., total pressure or total mass flow rate. As an alternative, the distribution of the flow in the individual parallel fluid paths may be corrected by actuating micro-valves in the individual fluid paths or by locally shifting the active area, for example, by a local temperature change. The latter is indicated particularly in strongly exothermic or endothermic reactions because such reactions, without a correction, strongly tend to accelerate the change.

The fluid paths being monitored by sensors at the same respective locations can be parallel micro-channels in a micro-fluidic component, e.g., a micro-reactor.

In micro-fluidic systems in which entire micro-fluidic components, or systems assembled from micro-fluidic components, are connected in parallel, the monitoring refers to the respective parallel-connected micro-fluidic components or systems. This means that the monitored fluid paths are the fluid-conducting structures in the individual parallel-connected micro-fluidic components. Of course, the fluid-conducting structures can in turn also have parallel micro-channels, which can be monitored in the same manner as described above.

The sensors can be, for example, pressure sensors that measure the pressures at the same locations in each of the fluid paths. The reference pressure can be the input pressure or output pressure of the fluid at the input or output of the parallel connection, such that, in the event of an obstruction of the fluid path, it can be determined whether the obstruction is located between the input and the site of the pressure measurement or between the site of the pressure measurement and the output.

Alternatively, the sensors can be temperature sensors that measure the temperatures in the environment of the parallel fluid paths at the same respective locations. If the mass flow rates through the fluid paths differ, then temperature differences result, which indicate a change in the operating state.

Another possibility for monitoring is to measure the mechanical stresses in the environment of the parallel fluid paths. Because of pressure and/or temperature differences in the individual fluid paths, different mechanical stresses can occur at the different locations.

It is of course also possible to provide several sensors of the same type for each fluid path at different locations, or even different sensors for measuring different physical or chemical parameters, to enable a more precise localization of the faults and to make the monitoring more reliable overall.

The parallel connection of micro-fluidic components, or systems of micro-fluidic components, has the advantage that one micro-fluidic component can work respectively as a master and the other parallel micro-fluidic components as slaves. The slaves each have a reduced sensor sophistication compared to the master, and the evaluation unit connected to the sensors diagnoses changes in the operating state of the slaves in relation to the master. While the master is equipped with a complete set of sensors to fully control a process or partial process, the sensor equipment of the slaves is reduced to a minimum. The settings made by the master in connection with the process control, e.g., control commands for control valves, are adopted by the slaves, so that the same operating states are set with respect to the slaves as with respect to the master. In this case, the evaluation unit connected to the sensors merely monitors whether the operating states of the slaves differ from those of the master. This makes it possible to significantly reduce the complexity and cost of the sensor technology in a parallelized micro-fluidic system.

BRIEF DESCRIPTION OF THE DRAWINGS

The invention will now be described in greater detail with reference to the drawing, in which.

DETAILED DESCRIPTION OF THE PREFERRED EMBODIMENTS

Figure 1:
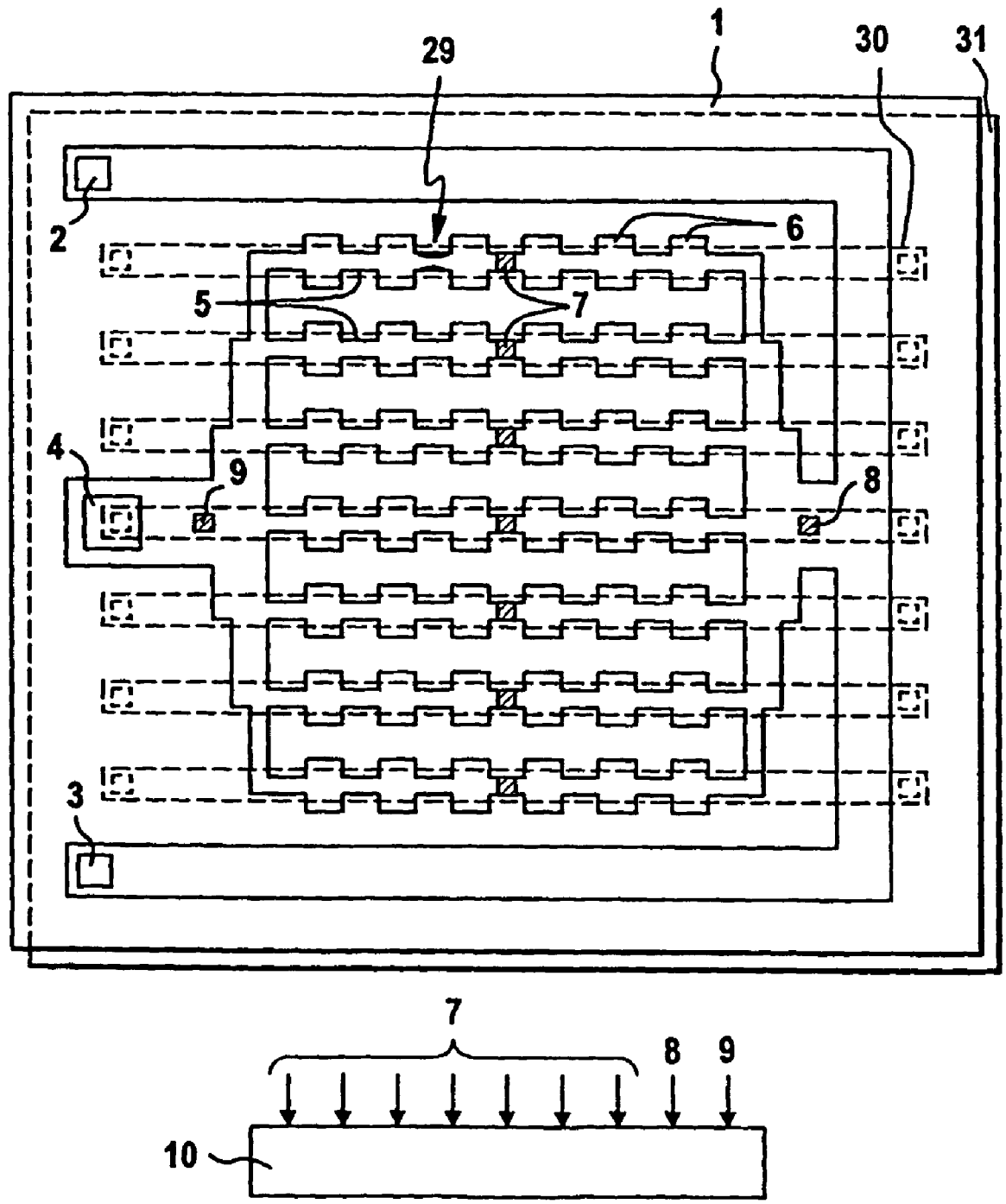
FIG. 1 shows a micro-fluidic component with parallel micro-channels, which are monitored by sensors and an evaluation unit connected thereto.

FIG. 1 shows a micro-fluidic component, in this case e.g. a mixer or reactor, in which a plurality of parallel, mutually similar micro-channels 5 are formed. These micro-channels 5 are arranged between two inputs 2 and 3 for two fluids to be mixed and an output 4 for the product being produced by mixing. In these micro-channels 5, the two combined fluids are mixed in successive mixing stages 6 and may react in the process.

Each of the micro-channels 5 has, for example, a pressure sensor 7, which is disposed, in this embodiment, midway in the center. The pressure sensors 7 and two additional pressure sensors 8 and 9 for measuring the input and output pressures of the micro-fluidic component 1 are connected to an evaluation unit 10. In an undisturbed operating state, the same process conditions exist in the separate micro-channels 5, such that the pressures measured by the sensors 7 are respectively the same. In relation to the input pressure measured by the pressure sensor 8 or the output pressure measured by the pressure sensor 9, the pressures measured by the sensors 7 each equal half the total pressure drop across the micro-channels 5. If one of the micro-channels 5 is completely obstructed, e.g., at the location identified by 29, then the associated pressure sensor 7 measures the same pressure as the pressure sensor 8, such that the pressure difference between the associated sensor 7 and the sensor 8 is zero and between the sensor 7 and the sensor 9 equals the total pressure drop across the micro-channels 5. Thus, the evaluation unit 10 can diagnose changes in the operating state of the micro-fluidic component 1 and localize faults in the individual micro-channels 5 based on pressure differences measured by the sensors 7.

If a respective pressure sensor 7 is arranged between each of the mixing stages 6, (not explicitly shown in FIG. 1 but nonetheless apparent and thus disclosed), the faults can be localized even more precisely. The effects of an incipient obstruction in one of the micro-channels 5, i.e., an obstruction that is not yet complete, can be compensated, for example, by additionally heating the micro-fluidic component 1 at the site of the affected micro-channel 5. For this purpose, the micro-channels 5 can be assigned, for example, additional channels 30 of a heat exchanger 31, which can be switched individually via micro-valves (not depicted) to permit different heating or cooling of the individual micro-channels 5.

Figure 2:
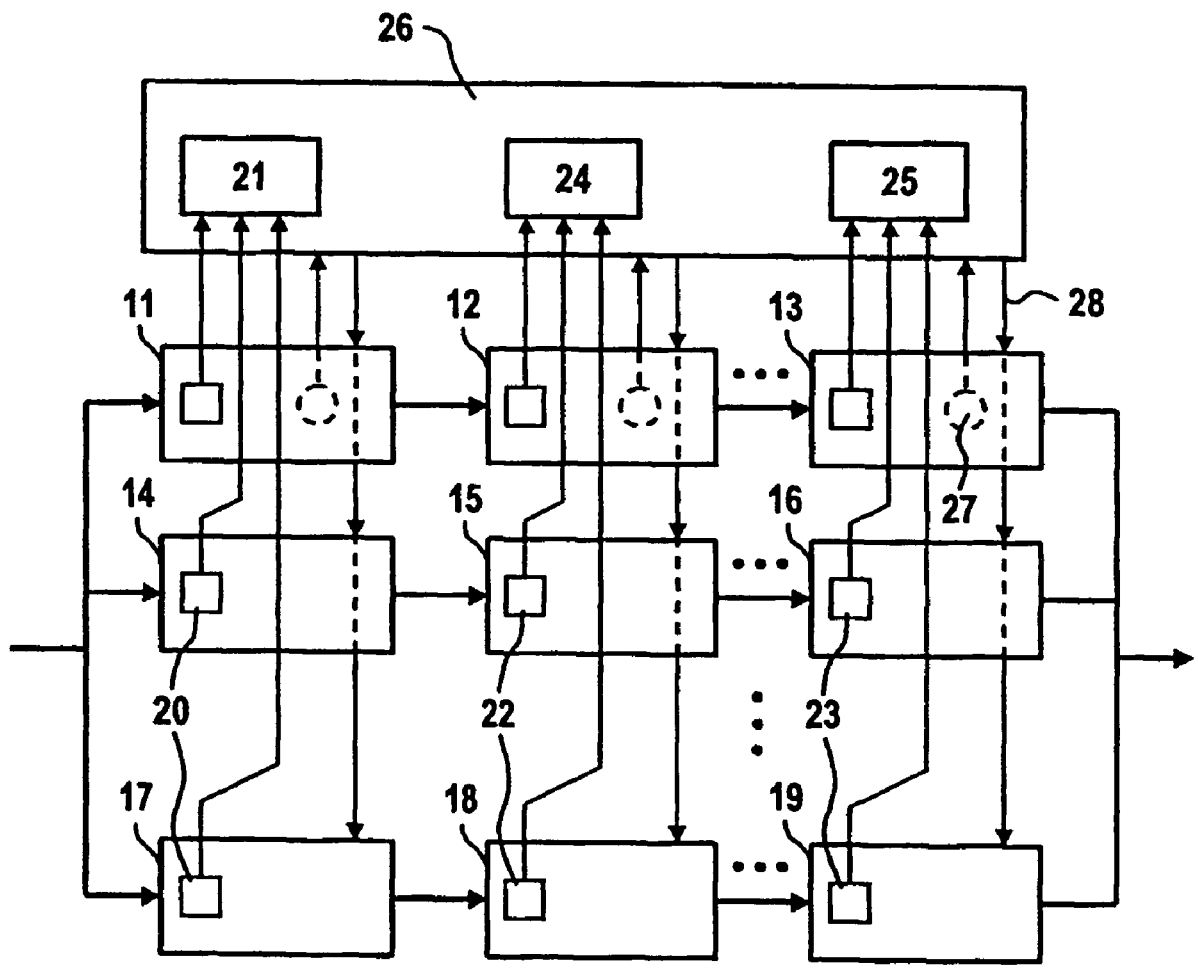
FIG. 2 shows a parallelized micro-fluidic system assembled from a plurality of micro-fluidic components, in which the respective parallel micro-fluidic components are monitored by sensors and an evaluation unit connected thereto.

FIG. 2 shows a parallelized micro-fluidic system in which other similar systems with micro-fluidic components 14, 15, 16 and 17, 18, 19 are connected to a first system with successive micro-fluidic components 11, 12, 13. The micro-fluidic components 11, 14, 17 are each mutually analogously fashioned. The same is true for the micro-fluidic components 12, 15, 18 and, respectively, 13, 16, 19. The micro-fluidic components 11, 14, 17 each have a sensor 20 at the same location, for example a temperature sensor, which is connected to an evaluation unit 21. The other micro-fluidic components 12, 15, 18 and 13, 16, 19 are likewise provided with sensors 22 and 23, which are connected to evaluation units 24 and 25. As long as the micro-fluidic system operates without error, the process conditions in the corresponding parallel micro-fluidic components, e.g., 11, 14, 17, are identical, such that the associated sensors 20 each measure the same value for the physical quantity, in this case temperature. If a fault occurs in one of the micro-fluidic components, e.g., 17, the change in the mass flow rate through the corresponding micro-fluidic component 17 will cause a change in the temperature measured there, such that the evaluation unit 21 diagnoses a change in the operating state of the micro-fluidic component 17 based on the difference of the corresponding temperature relative to the temperatures measured in the other micro-fluidic components 11 and 14. The micro-fluidic components 13, 16, 19 are, for example, mixers or reactors. The sensors 23 monitor, for example, the pH value of the mixed fluids and thus their mixing ratio.

In the depicted example, the evaluation units 21, 24 and 25 form part of a device 26 to control and regulate the process running in the micro-fluidic system. The system consisting of the micro-fluidic components 11, 12 and 13 is configured as the master, while the systems consisting of the micro-fluidic components 14, 15, 16 and, respectively, 17, 18, 19, work as slaves. The micro-fluidic components 11, 12, 13 of the master are equipped with a complete set of sensors 27 and report the measured process states to the device 26. Compared to the master, the micro-fluidic components 14, 15, 16 and 17, 18, 19 of the slaves are equipped only with a reduced set of sensors. Here this is expressed in a greatly simplified manner by the fact that they do not report any process states to the device 26. Based on the process states measured by the set of sensors 27 of the master, the device 26 generates control commands 28 for both the micro-fluidic components 11, 12, 13 of the master and the micro-fluidic components 14, 15, 16 and 17, 18, 19 of the slaves. As a result, the same operating states are adjusted in the micro-fluidic components of the slaves as in the master. The evaluation units 21, 24, 25 then only monitor whether the operating states in the micro-fluidic components of the slaves differ from those of the master.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. A parallelized micro-fluidic system, comprising:
   a plurality of mutually similar fluid paths connected in parallel, wherein the plurality of paths are branched from a common input point and later merged at an output point, the plurality of mutually similar fluid paths having a first undisturbed state in which none of the mutually similar fluid paths are clogged or fouled and a second disturbed state in which at least one of the mutually similar fluid paths is fouled or clogged, wherein in the first undisturbed state a same mass rate of flow is present in all the parallel-connected fluid paths;
   sensors configured to measure at least one physical or chemical parameter influenced by a fluid stream in the fluid paths and respectively assigned to fluid paths at corresponding respective locations of the fluid paths, wherein in the first undisturbed state the measured parameters are respectively same in value; and
   an evaluation unit connected to the sensors and configured to evaluate a change in the operating state of the micro-fluidic system based on at least the parameter measured in at least one of the fluid paths in the second disturbed state differing in value from the parameters measured in the other ones of the fluid paths in the second disturbed state.

2. The micro-fluidic system as claimed in claim 1, wherein the fluid paths comprise micro-channels, arranged mutually in parallel, of a micro-fluidic component.

3. The micro-fluidic system as claimed in claim 1, wherein the fluid paths comprise fluid conducting structures in homogenous micro-fluidic components arranged mutually in parallel.

4. The micro-fluidic system as claimed in claim 1, wherein the sensors are configured to measure pressures in the fluid paths at the corresponding respective locations.

5. The micro-fluidic system as claimed in claim 1, wherein the sensors are configured to measure temperatures at the corresponding respective locations.

6. The micro-fluidic system as claimed in claim 1, wherein the sensors are configured to measure mechanical stresses at the corresponding respective locations.

7. The micro-fluidic system as claimed in claim 1,
   wherein the fluid paths comprise at least one group of micro-fluidic components arranged mutually in parallel;
   wherein one of the micro-fluidic components of the group is configured as a master, and remaining ones of the micro-fluidic components of the group are configured as slaves;
   wherein the slaves each have less sensor complexity than the master; and
   wherein the evaluation unit connected to the sensors evaluates comparative changes in operating states of the slaves in relation to an operating state of the master.

8. A method for monitoring operation of a micro-fluidic system having plural fluid conduit branches, comprising:
   measuring, at a plurality of locations in the micro-fluidic system, at least one physical or chemical parameter of a fluid passing through mutually similar plural branches of the micro-fluidic system connected in parallel
   wherein the plurality of paths are branched from a common input point and later merged at an output point such that the plurality of mutually similar fluid paths have a first undisturbed state in which none of the mutually similar fluid paths are clogged or fouled and a second disturbed state in which at least one of the mutually similar fluid paths is fouled or clogged, wherein in the first undisturbed state the mass rate of flow is present in all parallel connected fluid branches,
   wherein the locations include at least one measuring site from each of the plural branches, and
   wherein the measuring sites are mutually analogous at least with regard to the measured parameter, in order to provide a plurality of measured values indicative of the parameter at the respective measuring sites,
   wherein in the first undisturbed state the measured parameters are respectively same in value, and
   evaluating the measured values for changes indicative of a change in operation of the micro-fluidic system, the evaluation being based on at least one measured parameter differing in value from other measured parameters in the second state.

9. The method according to claim 8, wherein said evaluating comprises evaluating for changes in at least one of the measured values relative to at least one other of the measured values.

* * * * *